United States Patent [19]

Yale

[11] 3,956,493

[45] May 11, 1976

[54] LONG ACTING TRANQUILIZING AGENT

[75] Inventor: Harry L. Yale, New Brunswick, N.J.

[73] Assignee: E. R. Squibb & Sons, Inc., Princeton, N.J.

[22] Filed: Oct. 21, 1974

[21] Appl. No.: 516,701

[52] U.S. Cl............................ 424/247; 260/243 A
[51] Int. Cl.² ................................... C07D 279/30
[58] Field of Search................ 260/243 A; 424/247

[56] References Cited
UNITED STATES PATENTS

| 3,320,248 | 5/1967 | Bernstein | 260/243 A |
| 3,320,249 | 5/1967 | Bernstein | 260/243 A |
| 3,627,759 | 12/1971 | Blondel et al | 260/243 A |
| 3,875,156 | 1/1975 | Blondel et al | 260/243 A |

OTHER PUBLICATIONS

Hawley, The Condensed Chemical Dictionary, 8th Ed., Frontispage and p. 923, Van Nostrand Reinhold Co., NY, (1971).
Jilek et al. Collection Czechoslov. Chem. Commun., Vol. 38, pp. 1190 to 1199, (1973).

*Primary Examiner*—John D. Randolph
*Attorney, Agent, or Firm*—Lawrence S. Levinson; Merle J. Smith

[57] ABSTRACT

1-Adamantanecarboxylic acid ester of pipotiazine is a long acting derivative of the tranquilizing agent.

4 Claims, No Drawings

LONG ACTING TRANQUILIZING AGENT

DETAILED DESCRIPTION OF THE INVENTION

Pipotiazine [10-[3-[4-(2-hydroxyethyl)piperidino]propyl]-N,N-dimethylphenothiazine-2-sulfonamide] and its carbonate esters, among a larger group of phenothiazine derivatives, are disclosed as long-acting neuroleptics, anti-emetics and tranquilizers in U.S. Pat. No. 3,627,759. The palmitate is shown in USAN 10(1974); see also 182 USPQ 294.

It has now been found that a new long acting derivative of pipotiazine, the 1-adamantanecarboxylic acid ester of pipotiazine, i.e., 10-[3-[4-(2-hydroxyethyl)-piperidino]propyl]-N,N-dimethylphenothiazine-2sulfonamide-b 1-adamantanoate, is a long acting tranquilizer having a duration of activity up to 7 weeks.

The new ester of this invention is produced by reacting pipotiazine with a 1-adamantoyl halide like the chloride in an anhydrous organic solvent, e.g., an aromatic hydrocarbon like benzene, toluene, xylene, cymene, cumene, mesitylene, or the like, in the presence of an acid acceptor, e.g., an organic amine such as a lower alkylamine like triethylamine, tributylamine, ethyl-diisopropylamine, N-methylmorpholine or the like. Heat, e.g., up to reflux temperature, is preferably applied to the reaction mixture.

After removal of the organic amine hydrochloride formed as a byproduct, the product ester is purified by crystallizing in the form of a salt such as the oxalic salt, then neutralizing the salt, e.g., with sodium bicarbonate, to regain the free ester.

Further details of the synthesis are found in the examples below.

The 1-adamantanecarboxylic acid ester of pipotiazine is readily soluble in suitable vehicles, e.g., vegetable oils like sesame oil or coconut oil, and such solutions, at a concentration of 25 mg. of the ester in 1 ml. of the vehicle, are readily sterilized. They are administered subcutaneously, intramuscularly, or intraperitoneally at a dosage of 0.13 to 4.0 mg. per kg., preferably at a dose of 0.5 mg. per kg. by the indicated route. A rapid onset of activity is noted, employing one of several conditioned avoidance procedures in the rat or the monkey. Thus this ester of pipotiazine is useful for its tranquilizing effect in the treatment of chronic schizophrenia in various mammalian subjects. A single dose, in the range specified, exerts its effect for about 7 weeks.

The following examples are illustrative of the invention. All temperatures are in degrees celsius.

EXAMPLE 1

To 9.92 g. of 2-dimethylsulfamoyl-10-[3-[4-(2-hydroxyethyl)piperidino]propyl]phenothiazine in 225 ml. of anhydrous benzene is added 4.37 g. of 1-adamantoyl chloride, followed by the dropwise addition of 3.5 ml. of triethylamine. The mixture is refluxed for 26 hours, filtered from triethylamine hydrochloride, and the benzene filtrate concentrated to dryness in vacuo. The residual oil does not crystallize.

To a solution of the oil, 15.32 g., in 100 ml. of Reagent Grade acetone, at the boiling point, is added a boiling solution of 4.77 g. of oxalic acid in 50 ml. of Reagent Grade acetone, rapidly and with thorough mixing. The clear solution that forms, gradually deposits large granules of the mono-oxalic acid salt, m.p. 154°–155° (dec.). It is recrystallized from acetone to give the purified product, m.p. unchanged at 154°–155° (dec.).

EXAMPLE 2

The oxalic acid salt, 14.6 g., as obtained in Example 1, is distributed between a solution of 5.0 g. of sodium bicarbonate in 100 ml. of water and 250 ml. of ether, with agitation. When two clear phases are formed, the ether layer is separated, the water layer is reextracted with 2 × 25 ml. portions of ether, and the ether solutions are combined. The combined ether solution is washed with 25 ml. of water, 25 ml. of saturated aqueous sodium chloride, dried, and concentrated to give 10-[3-[4-(2-hydroxyethyl)-piperidino]propyl]-N,N-dimethylphenothiazine-2-sulfonamide-1-adamantanoate (1-adamantanecarboxylic acid ester of pipotiazine) as a pale yellow oil.

EXAMPLE 3

A solution for injection is produced by dissolving 25 gm. of the 1-adamantanecarboxylic acid ester of pipotiazine in 1 liter of sesame oil with thorough mixing. The solution is sterilized, subdivided into sterile vials each containing 25 mg. in 1 ml. of oil solution and sealed.

What is claimed is:

1. 1-Adamantanecarboxylic acid ester of pipotiazine.
2. A composition comprising 1-adamantanecarboxylic acid ester of pipotiazine in a physiologically acceptable vehicle therefor.
3. A composition as in claim 2 wherein the vehicle is vegetable oil.
4. A composition as in claim 2 wherein the vehicle is sesame oil.

* * * * *